United States Patent
Quartey

(10) Patent No.: US 10,149,858 B2
(45) Date of Patent: Dec. 11, 2018

(54) TREATMENT FOR MIGRAINE

(71) Applicant: Kingsley Yianomah Quartey, Toronto (CA)

(72) Inventor: Kingsley Yianomah Quartey, Toronto (CA)

(*) Notice: Subject to any disclaimer, the term of this patent is extended or adjusted under 35 U.S.C. 154(b) by 0 days.

(21) Appl. No.: 14/992,955

(22) Filed: Jan. 11, 2016

(65) Prior Publication Data

US 2016/0143936 A1    May 26, 2016

Related U.S. Application Data

(63) Continuation-in-part of application No. 13/590,134, filed on Aug. 20, 2012.

(51) Int. Cl.
| | |
|---|---|
| *A61K 36/24* | (2006.01) |
| *A61K 31/7048* | (2006.01) |
| *A61K 9/00* | (2006.01) |
| *A61K 9/10* | (2006.01) |
| *A61K 9/107* | (2006.01) |
| *A61K 47/38* | (2006.01) |

(52) U.S. Cl.
CPC ........ *A61K 31/7048* (2013.01); *A61K 9/0043* (2013.01); *A61K 9/10* (2013.01); *A61K 9/107* (2013.01); *A61K 36/24* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 2003/0229029 A1* | 12/2003 | Laudadio | ............... | A61K 31/60 514/26 |
| 2004/0082521 A1* | 4/2004 | Singh | ................... | A61K 9/1271 514/26 |
| 2005/0026849 A1* | 2/2005 | Singh | ................. | A61K 31/7048 514/26 |
| 2006/0205679 A1* | 9/2006 | Streeper | ............. | A61K 31/7048 514/26 |
| 2009/0318374 A1* | 12/2009 | Harrington | ............ | A61K 31/00 514/26 |
| 2012/0077763 A1* | 3/2012 | O'Rourke | ............ | A61K 31/553 514/26 |

* cited by examiner

*Primary Examiner* — Christopher R Tate
(74) *Attorney, Agent, or Firm* — Donald S Debelak

(57) ABSTRACT

The present invention relates to methods for the treatment of migraine headache, cluster headache, tension type headache, trigeminal neuralgia (trigeminal headache) and headache disorders. The methods comprise administration of specific cardiac glycosides: Thevetin A and or Thevetin B to a subject in need thereof a pharmaceutically suitable preparation, in the form of nasal spray and or other modes and methods that will ensure adequate intranasal dosage, a pharmaceutically suitable preparation of the said cardiac glycosides that is sufficient to have the most desirable therapeutic effect when used as a prophylaxis, as a treatment and ameliorating agent of migraine headache and others headache disorders.

5 Claims, No Drawings

TREATMENT FOR MIGRAINE

CROSS REFERENCED TO A RELATED PATENT APPLICATION

This application is a Continuation in Part Application of U.S. patent application Ser. No. 13/590,134, filed Aug. 20, 2012

CITATIONS

U.S. patent application Ser. No. 12/298,254 Publication Number US20090318374 A1
Also published as:
EP2013626A2, U.S. Pat. No. 8,163,270, US20120270816, WO2007127237A2, WO2007127237A3
(Sayani A P and Chien Y W (1996) Critical Reviews in Therapeutic Drug Carrier Systems, 12:85-184
Global Year Against HEADACHE October 2011-October 2012
Science Daily May 21, 2014
(www.sciencedaily.com/releases/2014/05/140521133603.htm)

BACKGROUND OF THE INVENTION

1. Field of the Invention.

The present invention relates generally to methods and compositions for the treatment of migraine headaches, trigeminal neuralgia, headaches, and headache disorders. More specifically, the present invention relates to methods of treating migraine headaches, trigeminal neuralgia, headaches and head pain disorders by administering a pharmaceutically suitable composition made with and or containing Thevetin A and or Thevetin B in the form of a nasal spray, or other mode of packaging and administered intranasally. In particular the present invention relates to methods for the treatment and or prophylaxis of migraine headache (migraine), cluster headache, tension type headaches, headache disorders, head pain or trigeminal neuralgia, by administration of Thevetin A and or Thevetin B or a pharmaceutical composition comprising Thevetin A and or Thevetin B to individuals in need of treatment thereof.

2. Description of Related Art

There have been several published literature and patents disclosures that list methods of treating some forms of primary headaches using plants extracts that contains various levels of one or more cardiac glycosides and as expected other bioactive compounds. There are also numerous published literatures that teach the administration of drugs intranasally to treat headaches, neurological disorders and other brain diseases. Example is an article that was published by ScienceDaily, "Breakthroug: Nasal spray may soon replace pills for delivering drugs to the brain" ScienceDaily, 21 May, 2014. This particular article cites a study by Massimilano Di Cagno, Assistant Professor of Department of Physics, Chemistry and Pharmacy at the University of Southern Denmark, who in the article cited above, allegedly advocate the treatment of certain brain diseases by administering drugs intranasally. In the article Massimilano Di Cagno allegedly stated in that "People with brain diseases are often given huge amounts of unnecessary drugs. During a long life, or if you have a chronic disease, this may become problematic to your health". Massimilano Di Cagno and his colleagues are said to have tested a natural sugar and they reported said that this particular polymer is not only capable of carrying drugs through the nasal wall but also most importantly—releasing the drug where it is needed. "This is an important breakthrough, which will bring us closer to delivering brain drugs by nasal spray" Missimilano Di Cagno, added to his statement. The implication being that pharmaceutical drugs that are used to trait brain related disorders can be administered intranasally or as a nasal spray.

The medicinal use of plants extracts that contains various cardiac glycosides are in published literature. Example, the esteemed journal Bothalia which has been in publication since 1921, and is now publishedas "The African Biodiversity & Conservation", teaches in PROTA 11 (1)—Bothalia 7: 448, that the plant *Acokanthera oppositifolia* (also known as "Bushman poison" in English and "Msungu" in Swahili) which contains cardiac glycosides "In South Africa root powder or leaf powder is sniffed to cure headache, while leaf infusion is used as a nasal spray for the same purpose". Another example of the use of cardiac glycosides as a treatment is the United Patent US-2009/0318374 A1, Harrington (Michael G. Harrington) et al cites the use of various cardiac glycosides intranasally as a method for treating headache, without specifically mentioning Thevetin A and Thevetin B; and we also know that as of date, there is no cure for migraine headache, this makes this distinct invention worthy. No literature or patent(s), both published and or cited herein specifically mentions the use of Thevetin A and or Thevetin B, when used, example, in a pharmaceutically suitable preparation, and used intranasally (eg., a nasal spray) can be used as a treatment for migraine headache or other headaches.

BACKGROUND OF INVENTION

Current Treatments (Migraine)

There are many treatment regimes utilized for migraine headache and symptoms associated with migraine (example nausea), from Preventive treatment (prophylaxis type of treatment that tries to stop the migraine headache from occurring), Acute treatment (treating the migraine headache as soon as they occur) and Rescue treatment (dealing with the migraine headache attack, if the acute treatment does not work), although it is important to note that Triptans are a family of tryptamine-based drugs including but not limited to Sumatriptan, Rizatriptan, Naratriptan, Zolmitripan, Eletripan, Almotripan, Frovatripan, Avitripan and Donitripan, does enjoys a limited measure of success as a treatment option that is used as an abortive medication to treat migraine headache, however, to date there is no single treatment strategy (including prophylaxis) that successfully alleviates migraine in majority of the patients that have migraine headache. And it is important to note that Triptans are not considered as a cure for migraine headache. Some NSAID (Non-Steroidal Anti Inflammatory Drugs), Acetominophen, Acetyl Salicyclic Acid (Aspirin) or Aspirin in combination with caffeine (example "Excedrin Migraine") have all been marketed and utilized as migraine headache treatment, however, in most cases they offer very limited measure of success when employed against migraine and to this date it is generally accepted that there is no cure or treatment for migraine headache that will give migraine sufferers sustained relief from migraine headache to the point whereby they may feel cure or be able to go about their daily activities without being disabled by the migraine headache during a migraine attack.

One of the treatment options for treating migraine headache is migraine surgery. The surgical procedure is often undertaken with the aim of reducing or as a prophylaxis for migraine headache, however, because no accurate estimate exist about the efficacy of migraine surgery as an effective treatment of migraine headache, it is not considered a cure or an effective treatment for migraine headache, especially given the inherently high risks associated with the surgery. It is clear that to date there is no treatment for migraine headaches, cluster headaches and tension type headaches that can offer effective treatment and or relief to the point that the migraine headache, cluster headache or tension type headache is no longer considered by the patient to be a disability, or cure from these disabling conditions.

Current Treatments (Cluster Headache)

Currently there is no cure for cluster headaches. The goal of any treatment headache is to decrease the severity of the pain and shorten the duration of the headache and as a prophylaxis that may prevent onset of a cluster headache attack. There are acute treatments that are used to give some relief from cluster headache pains, and while they are not considered a cure, these acute treatments include but not limited to Oxygen; when 100% oxygen is administered through a mask to a person having an episode of cluster headache attack offers some relief, however, although there are portable oxygen cylinders currently available, many consider carrying an oxygen cylinder and the regulator that comes with its as impractical to use or carry with them. Injectable form of sumatripan (Imitrex), which is currently used against some forms of migraine headache has been as treatment for cluster headache, however, it takes time for its impact to be notice by the patient and because it is administered intravenously at a physician office, the added inconvenience of going to a clinical settings for a treatment makes some patients reluctant to engage in a treatment regime that requires so many steps. Additionally, though the treatment itself may give some temporal relief from cluster headache it is not considered a cure.

Current Treatments (Tension Headache)

Currently several OTC (Over the Counter) pain medications such as Aspirin, Ibuprofen (Non-Steroidal Anti Inflammatory Drugs) and prescription medications, including but not limited to naproxen, indomethacin and as well as Triptans and narcotics including opiates are used to treat Tension headaches, and while they offer some form of relive, for example some of the narcotics used to treat Tension headaches such as opiates can be habit forming.

Also NSAIDs (Non-steroidal Drugs) including those used to treat tension type headache, such as for example, Indomethacin, can increase cardiovascular thrombotic events, including increased risk for myocardial infarctions and stroke.

Current Treatments (Hemicrania Continua)

Hemicrania continua headache responds favorably to Indomethacin (Indomethacin is non-steroidal inflammatory drug) and other NSAID drugs, however, Indomethacin and the other pharmaceutical drugs when used to treat Hemicrania continua must administered on daily basis for long periods of time, and by administering those drugs to the patient for a long period increases the potential for cardiovascular thrombotic events, including increased risk for myocardial infarctions and stroke in the patient, making it undesirable.

Current Treatments (Trigeminal Neuralgia)

There are variety of treatment options for treating trigeminal neuralgia that may help reduce the rate of occurrence and the intensity of the pain, from using over the counter pain killers, prescription grade pain killers, anti-epileptic drugs, "Carbamazepine", to surgery, however, typical pain killers cannot effectively treat trigeminal neuralgia, and anti-epileptic drugs many known have undesirable side effects and surgery has inherent dangers that may make that treatment option unsuitable. There is no effective drug to this day that can cure trigeminal neuralgia.

BRIEF SUMMARY OF THE INVENTION

Provided herein are methods for preventing and treating migraine headache, tension type headache, trigeminal neuralgia, cluster headache, hemicrania continua, tension type headache and other primary type headaches comprising of administering an intranasally, a pharmaceutically suitable composition containing Thevetin A and or Thevetin B. Some aspects of the invention include methods whereby the said composition is administered as a nasal spray with or without excipients. Some aspects of the invention include methods whereby the said composition is delivered as a nasal spray powder with or without the aid of a propellant. Some aspects of the invention include methods whereby the headache is a primary headache or secondary headache. Some aspect of the invention includes methods of treating migraine associated headaches. Some aspects of the invention include methods of delivering the said composition via a nebulizer. Some aspects of the invention include excipients that allow uniform delivery of the treatment to patients in need of treatment thereof. Some aspects of the invention include adding excipients to the compound that will mask the taste thereby making it more convenient for patients to use.

DETAILED DESCRIPTION OF THE INVENTION

As used herein, and unless otherwise specified, the term "treatment" or "treating pain" regards to administration to an individual in need of treatment an agent of interest wherein the said agent alleviates or prevents a pathology for which the individual is being treated. "Treatment for headache pain", "treatment of headache", "treatment of head pain", "treatment of migraine", or treatment of migraine headache" refers to the treatment of migraine and associated headache disorders. Treatment for headache pain", "treatment of headache", "treatment of head pain", or "trigeminal neuralgia", refers to the treatment of trigeminal neuralgia and associated headache disorders. As used herein, and unless otherwise specified, the term "prevention", "prophylaxis" or "pain preventing" refers to administration to an individual of an agent of interest wherein the agent alleviates or prevents a pathology for which the individual is being treated. As used herein, "Thevetin A" and or "Thevetin B" are cardiac glycosides having biological activity that can be natural occurring and can also be man-made synthetic, its analogues or derivatives thereof. As used herein "migraine" includes migraine headache, migraine without aura, migraine with aura, and migraine with aura but without headache. As used herein; "surfactant" and "surfactants" refers to a substance that is utilized to reduce surface tension, and or used to increase the emulsification of two separate and distinct mediums, example, is emulsification of water and a lip substance such as oil.

Active Compounds

Cardiac glycosides are bioactive drug compounds, and the specific cardiac glycosides Thevetin A and or Thevetin B are drug compounds. Thevetin A and Thevetin B are often extracted together with other cardiac glycosides, namely, Peruvoside, Thevofolin, Oleandrin, Neriifolin and Thevetoxin from the White Oleander plant (*Thevetia Peruviana*) or the White Oleander plant (*Nerium Oleander*). Apart from the white oleander and the yellow oleander plants, there are other natural sources for Thevetin A and Thevetin B, including plant and animal sources, also Thevetin A and Thevetin B analogues, and synthetic man-made. Pure form of Thevetin A and Thevetin B are commercially available. Thevetin A is also known as Cannogenin 3-O-gentiobiosylthevetoside and Thevetin B is also known as Cerebroside.

Excepients

An excipient or excipients are natural or synthetic substances added alongside active ingredient of pharmaceutical drugs. The intended purpose of adding excipients to drugs is to act as diluents that dilutes and controls potency of the drug, preservatives that increase shelf life by retarding spoilage, acidulants and or alkalizing agents that adjust the pH to a more desirable level, flavors that improve taste, aftertaste and aroma, anti-oxidants that retards oxidation and increase shelf life, surfactants that increase the bioavailability of the active ingredient by reducing surface tension, bulking agent that helps control the bioavailability of the active drug compound and polymers that may help control the viscosity of the drug and improve uniform distribution of the drug, example when the drug contains ingredients with different level of solubility in the diluent, and glycols may also be added to prevent the dry-out of the drug and improve the overall comfort of the patient as well as improve the "plasticity" of the drug. Some excipients also improve the overall performance of the drug that they are included in. Example pharmaceutical grade of the surfactant Polysorbate-20 and its analogues are sometimes added to nasal spray to increase the "spray pattern" and "plume geometry" of the nasal spray, thereby improving it efficiency.

Art of Enablement, Sample Formulating and Sample Compounding

The following are examples of basic formulating and compounding examples for reference purposes only.

Nasal Spray (Suspension)

This invention relates to methods of treating migraine headaches and headache disorders by administering intranasally a pharmaceutically suitable preparation containing specific cardiac glycosides; Thevetin A and or Thevetin B intranasally in a form of a "Nasal Spray Suspension" to a patient in need of a treatment thereof.

Pharmaceutical suitable grades of:

Distilled Water (Diluent): 80%-99%

Sodium Carboxyl Methyl Cellulose (polymer and suspending agent): (q.s)

Microcrystalline Cellulose (polymer and suspending agent): (q.s)

Polysorbate-80 (surfactant and a spreading agent): quantum satis (q.s)

Sodium Benzoate or Benzalkonium Chloride (preservative agents): quantum satis (q.s)

Tocophyrol Acetate (Vit.E) (anti-oxidant): quantum satis (q.s)

EDTA (chelating agent): quantum satis (q.s)

Pharmaceutical Grade Thevetin A and or Thevetin B (active): quantum satis (q.s)

The distilled water be weighted into a cleaned stainless-steel vessel, and agitated until a vortex is formed, then the polymers (Sodium Carboxyl Methyl Cellulose and or Microcrystalline Cellulose) is weighed and slowly sprinkled into the vortex and mixed until a clear and a clean suspension mucilage without particulates is formed. The suspension is slowly heated to about 60° C. and the other ingredients are added, agitated and heated to 80° C. for about 30 minutes. The suspension is slowly cooled to room temperature of about 21° C., the suspension is then filtered and packaged into suitable packaged, example, nasal sprayers.

PS: "Quantum satis" or q.s. means "quantity sufficient but not exceeding".

Nasal Spray ("Dry Powder"):

This invention relates to methods of treating migraine headaches and headache disorders by administering intranasally a pharmaceutically suitable preparation containing specific cardiac glycosides: Thevetin A and or Thevetin B intranasally in a form of a "Nasal Spray Dry Powder" to a patient in need of treatment thereof.

Pharmaceutical suitable grades of

Oleic Add (bulking agent): q.s

Dextrose (bulking agent): q.s

Polysorbate 80 (surfactant): q.s.

Thevetin A and or Thevetin q.s

"Propellant" (Tetrafluoroethane): q.s.

The ingredients are weighted and added blended in a "powder mixer" such as "guttered mixer" then the "batch" is transferred to a stainless-steel jet mill or other suitable implement, where it is milled and micronized until a suitable particle size and uniformity is obtained. Example of a good particle size for this particular instance would be 6 microns. After the desirable particle size is obtained, the admixture is then packaged into a pressurized metered-dose aerosol units or non-pressurized metered dose units.

PS: "Quantum satis" or q.s. means "quantity sufficient but not exceeding".

Art of Enablement, Sample Formulating and Sample Compounding

The following are examples of basic formulating and compounding examples for reference purposes only.

Nebulizer (Suspension)

This invention relates to methods of treating migraine headaches and headache disorders by administering intranasally a pharmaceutically suitable preparation containing specific cardiac glycosides: Thevetin A and or Thevetin B intranasally via a "nebulizer" to a patient in need of treatment thereof.

Pharmaceutical suitable grades of

Distilled Water (Diluent): 80%-99% (or q.s)

Sodium Carboxyl Methyl Cellulose (polymer and suspending agent): (q.s)

Microcrystalline Cellulose (polymer and suspending agent): (q.s)

Polysorbate-80 (surfactant and a spreading agent): quantum satis (q.s)

Sodium Benzoate or Benzalkonium Chloride (preservative agents): quantum satis (q.s)

Tocophyrol Acetate (Vit.E) (anti-oxidant): quantum satis (q.s)

Flavoring Agent (Intransal suitable): (q.s)

Pharmaceutical Grade Thevetin A and or Thevetin B (active): quantum satis (q.s)

Example Compounding Method (For Reference Purpose Only)

The distilled water be weighted into a cleaned stainless steel vessel, and agitated with example an impeller mixer, until a vortex is formed, then the polymers (Sodium Carboxyl Methyl Cellulose and or Microcrystalline Cellulose) k weighed and slowly sprinkled into the vortex and mixed until a clear and a clean suspension mucilage without particulates is formed. The suspension is slowly heated to about 60 degrees C. and the other ingredients are added, agitated and heated to 80 degrees C. for about 30 minutes. The suspension is slowly cooled to room temperature of about 21 degrees C., the suspension is then filtered and packaged into Nebulizer or a suitable container and decanted into a nebulizer for use by a patient who due an illness or injury may not be able to a nasal spray or may not wish to use a nasal spray.

Art of Enablement, Sample Formulating and Sample Compounding

The following are examples of basic formulating and compounding examples for reference purposes only.

Nasal Spray (Emulsion)

This invention relates to methods of treating migraine headaches and headache disorders by administering intranasally a pharmaceutically suitable preparation containing specific cardiac glycosides: Thevetin A and or Thevetin B intranasally in a form of a "Nasal Spray Suspension" to a patient in need of treatment thereof.

Pharmaceutical suitable grades of:
Distilled Water (diluent): 80%-99%
Sodium Carboxyl Methyl Cellulose (polymer and suspending agent): (q.s)
Polysorbate-80 (surfactant and a spreading agent): quantum satis (q.s)
Glycerol Monostearate (CMS); quantum satis (q.s)
Mineral Oil (Parafin Oil); quantum satin (q.s)
Sodium Benzoate or Benzalkonium Chloride (preservative agents): quantum satis (q.s)
Tocophyrol Acetate (Vit.E) (anti-oxidant): quantum satis (q.s)
EDTA (chelating agent): quantum satis (q.s)
Pharmaceutical Grade Thevetin A and or Thevetin B (active): quantum satis (q.s)

The distilled water be weighted into a cleaned stainless-steel vessel, and agitated until a vortex is formed, then the polymers (Sodium Carboxyl Methyl Cellulose and or Microcrystalline Cellulose) is weighed and slowly sprinkled into the vortex and mixed until a clear and a clean suspension mucilage without particulates is formed. The water phase: the water and the C.M.0 and the oil phase (the light mineral oil, the polysorbate-80 and the G.M.S) are heated separately until about 80 degrees C., then one phase, example, the oil phase is added to the water phase, and agitated rapidly with an impeller mixer or other suitable mixer until an "emulsion" is formed. The emulsion is cooled to about 25 degrees C. and packaged in Nasal Spray, using piston fillers or other packaging machines.

Routes of Administration

This invention relates to methods of treating migraine headaches and related headaches, by administering to a patient in need of treatment thereof a pharmaceutically suitable preparation, containing specific cardiac glycosides: Thevetin A and or Thevetin B. The primary route of administering this invention is to use it as a nasal spray, either in a suspension "solution", suspension "emulsion" or "metered—dose dry powder method" which is also known as Dry Powder Inhaler or DPI, which is increasingly becoming more common as means of delivering active pharmaceutical drugs intranasally. However, should the patient be incapacitated or unwilling to use the drug intranasally as a nasal spray, a "special device" or delivered method, example, a "specifically designed or specifically calibrated" nebulizer can be prescribed by a physician to be employed in delivering the said invention to a patient in of treatment thereof. According to (Sayani A P and Chien Y W (1996) Critical Reviews in Therapeutic Drug Carrier Systems, 12:85-184—"Intranasal delivery has a number of advantageous features including comparatively high bioavailability, rapid kinetic of absorption and avoidance of a first-pass effect in the liver". In order to avoid hepatic first-pass metabolism, intranasal delivery of the treatment method described in this invention is ideal.

Dosage

The dosage of the invention, which relates to methods of treating migraine headaches and headache disorders by administering intranasally a pharmaceutically suitable preparation, containing the specific cardiac glycosides: Thevetin A and or Thevetin B, would depend on the age, weight, the overall health of the patient being treated and physician treating the patient, based on critical factors would determine how best to prescribe the said preparation. However, for example, an effective dose of about 1 mcg to 85 mcg of the active compound of Thevetin A and or Thevetin B in a 50 ml total volume of the said preparation when used by an adult of about 75 kg weight, is usually sufficient, when used twice or thrice daily as a nasal spray or when used nasally twice or thrice daily is very effective treatment for primary headaches, including migraine headache, trigeminal headache, cluster headache, tension type headache, hypnic headache. It is important to note that a regulatory body, the physician who prescribe the drug, and the legal constraints is what will ultimately establish the dosage level. Intranasally in this context means nasal spray or nasal drop, or other methods that will allow the said drug to be safely and effectively dosed via or through the nasal cavity. In another embodiment of the invention, between the percentage rate of 0.001 to 22% of Thevetin A and or Thevetin B in a pharmaceutically effective preparation administered intranasally and or in the form of nasal spray is sufficient to ameliorate, treat and a prophylaxis against migraine headaches and other primary headaches.

Derivative of an Active Ingredient

In chemistry a derivative is a compound that is derived from similar compound by some chemical or a physical process.

Example, according to Uber-Bucek E, Harron M, Pham Huy C, and Dadoun H (Laboratorie de Pharmacognosie, Faculty des Sciences, Chatenay Malabry, France) in the Journal of Pharmaceutical and Biomedical Analysis (1992, 10 (6): 413-419): "The cardiac glycoside Thevetin B genin is structurally identical to digitoxigenin". Another example of a chemical analogue is the comparison of the synthetic chemical compound "vanillin" and the natural vanillin. "Vanillin" which is synthetic may be produced as a by-product of wood alcohol or produced by using petrochemicals or as a by-product from the paper industry, is identical to the vanillin in vanilla beans, however, it is not obtained from the vanilla beans.

I claim:

1. A method for treating a migraine headache in a subject in need thereof, comprising intranasally administering to the subject a pharmaceutical composition comprising an effective and suitable amount of Thevetin A and/or Thevetin B.

2. The method according to claim 1, wherein the composition is in the form of a nasal spray.

3. The method according to claim 1, wherein the composition contains one or more excipients.

4. The method according to claim 1, wherein the composition contains Thevetin A.

5. The method according to claim 2, wherein the composition contains Thevetin B.

* * * * *